US00PP35120P2

(12) United States Plant Patent
Mathey

(10) Patent No.: US PP35,120 P2
(45) Date of Patent: Apr. 25, 2023

(54) ***WEIGELA* PLANT NAMED 'SMNWFG'**

(50) Latin Name: *Weigela florida*
Varietal Denomination: SMNWFG

(71) Applicant: Megan M. Mathey, Holland, MI (US)

(72) Inventor: Megan M. Mathey, Holland, MI (US)

(73) Assignee: SPRING MEADOW NURSERY INC., Grand Haven, MI (US)

( * ) Notice: Subject to any disclaimer, the term of this patent is extended or adjusted under 35 U.S.C. 154(b) by 0 days.

(21) Appl. No.: 17/953,103

(22) Filed: Sep. 26, 2022

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226

CPC ... A01H 5/02; A01H 5/12; A01H 5/00; A01H 6/00

See application file for complete search history.

(56) References Cited

U.S. PATENT DOCUMENTS

PP32,223 P2 * 9/2020 Wood ..... A01H 5/02 Plt./226

* cited by examiner

*Primary Examiner* — June Hwu
(74) *Attorney, Agent, or Firm* — C. Anne Whealy

(57) ABSTRACT

A new and distinct cultivar of *Weigela* plant named 'SMNWFG', characterized by its upright to outwardly spreading and uniformly mounding plant habit; vigorous growth habit and rapid growth rate; freely branching habit; dense and bushy appearance; leaves that are dark green in color tinged with dark reddish brown; freely and remontant flowering habit; bright purplish red-colored flowers; and good garden performance.

2 Drawing Sheets

Figure 1:
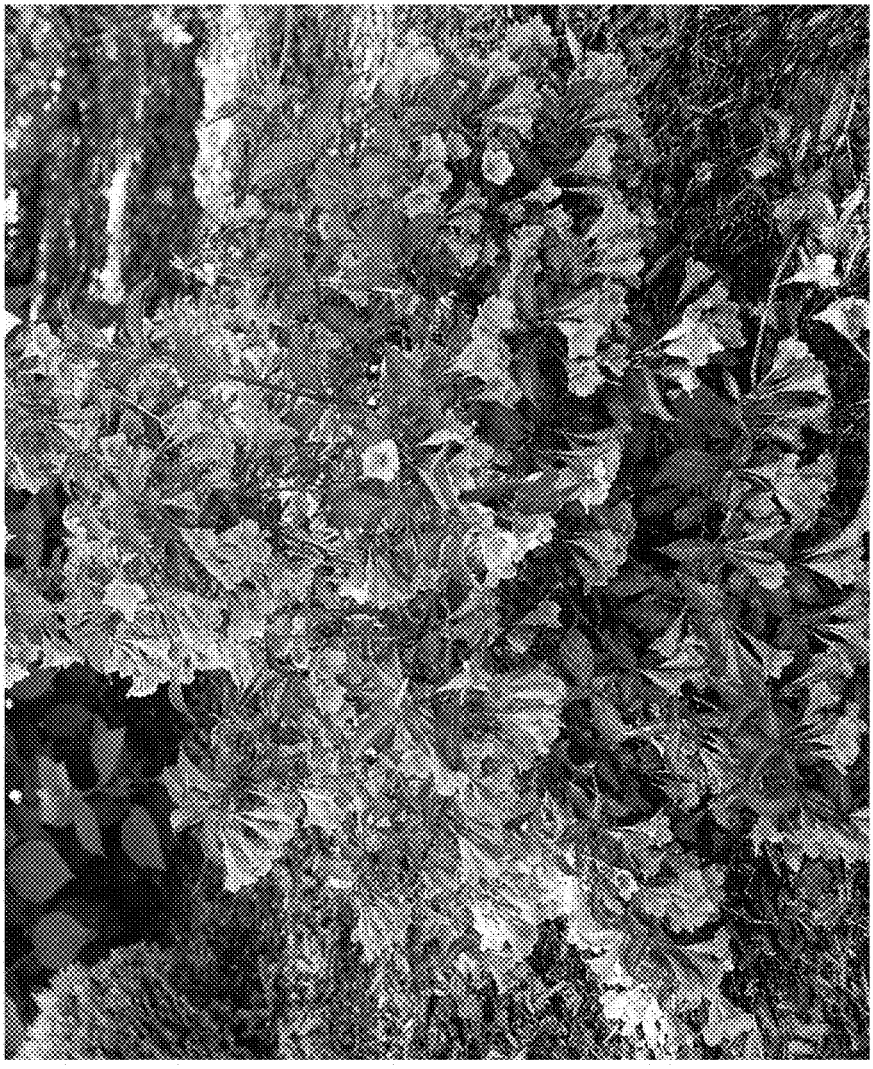

Botanical designation: *Weigela florida.*
Cultivar denomination: 'SMNWFG'.

BACKGROUND OF THE INVENTION

The present invention relates to a new and distinct cultivar of *Weigela* plant, botanically known as *Weigela florida* and hereinafter referred to by the name 'SMNWFG'.

The new *Weigela* plant is a product of a planned breeding program conducted by the Inventor in Grand Haven, Mich. The objective of the breeding program was to develop new compact *Weigela* plants with dark-colored leaves and freely and remontant flowering habit.

The new *Weigela* plant originated from an open-pollination in 2016 in Grand Haven, Mich. of an unnamed proprietary selection of *Weigela florida*, not patented, as the female, or seed, parent with an unknown proprietary selection of *Weigela florida* as the male, or pollen, parent. The new *Weigela* plant was discovered and selected by the Inventor in 2018 as a single flowering plant within the progeny of the stated open-pollination in a controlled environment in Grand Haven, Mich.

Asexual reproduction of the new *Weigela* plant by softwood stem cuttings since 2018 in Grand Haven, Mich. has shown that the unique features of this new *Weigela* plant are stable and reproduced true to type in successive generations of asexual reproduction.

SUMMARY OF THE INVENTION

Plants of the new *Weigela* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNWFG'. These characteristics in combination distinguish 'SMNWFG' as a new and distinct *Weigela* plant:

1. Upright to outwardly spreading and uniformly mounding plant habit.
2. Vigorous growth habit and rapid growth rate.
3. Freely branching habit; dense and bushy appearance.
4. Leaves that are dark green in color tinged with dark reddish brown.
5. Freely and remontant flowering habit.
6. Bright purplish red-colored flowers.
7. Good garden performance.

In side-by-side comparisons, plants of the new *Weigela* differ primarily from plants of the female parent selection in the following characteristics:

1. Leaves of plants of the new *Weigela* are dark green in color tinged with dark reddish brown whereas leaves of plants of the female parent selection are dark green in color, but not as darkly tinged.
2. Plants of the new *Weigela* flower more remontantly than plants of the female parent selection.

Plants of the new *Weigela* can also be compared to plants of the *Weigela florida* 'SMWFDFPD', disclosed in U.S. Plant Pat. No. 32,223. In side-by-side comparisons plants of the new *Weigela* differ primarily from plants of 'SMWFDFPD' in the following characteristics:

1. Under high light conditions, leaves of plants of the new *Weigela* are not as heavily tinged as leaves of plants of 'SMWFDFPD'.

2. Plants of the new *Weigela* flower more remontantly than plants of 'SMWFDFPD'.

BRIEF DESCRIPTION OF THE PHOTOGRAPHS

The accompanying colored photographs illustrate the overall appearance of the new *Weigela* plant showing the colors as true as it is reasonably possible to obtain in colored reproductions of this type. Colors in the photographs may differ slightly from the color values cited in the detailed botanical description which accurately describe the colors of the new *Weigela* plant.

The photograph on the first sheet (FIG. 1) is a side perspective view of a typical flowering plant of 'SMNWFG' grown in an outdoor nursery.

Figure 2:
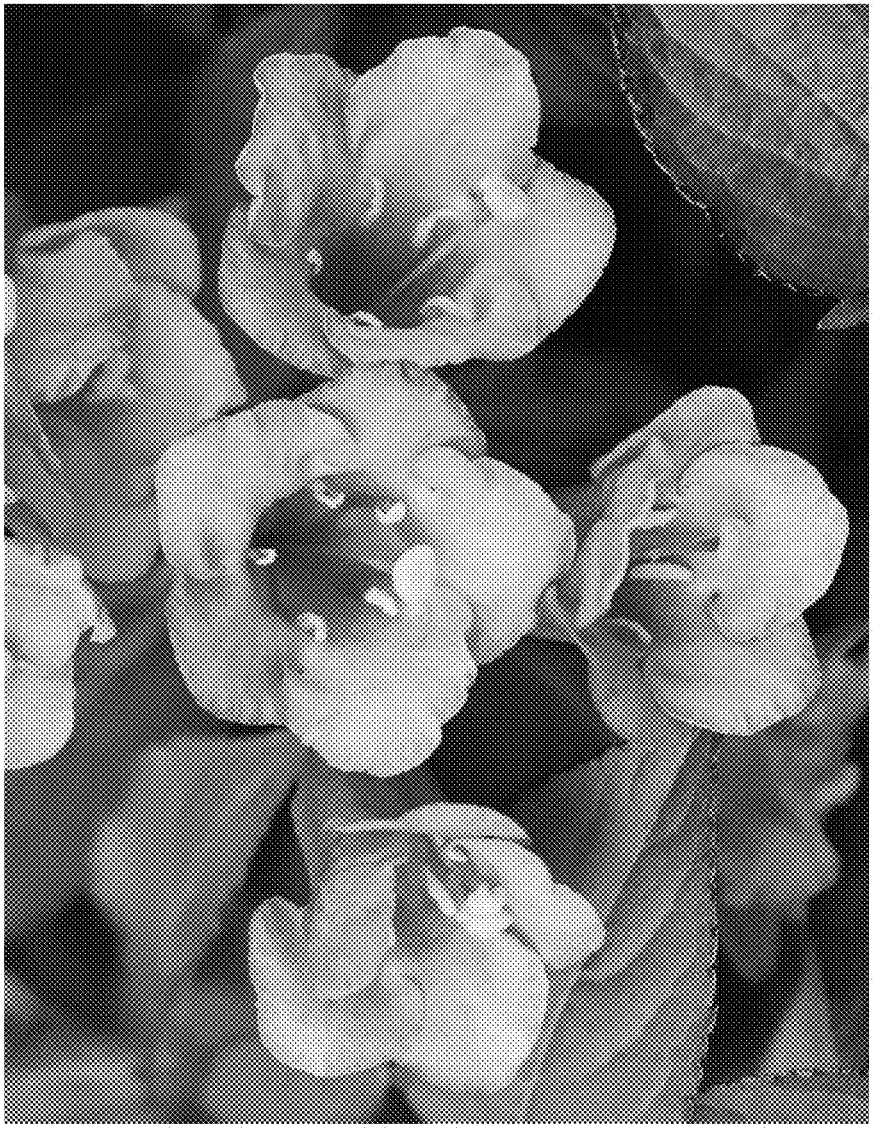

The photograph on the second sheet (FIG. 2) is a close-up view of typical flowers of 'SMNWFG'.

DETAILED BOTANICAL DESCRIPTION

Plants used for the aforementioned photographs and the following description were grown during the spring in ground beds in an outdoor nursery and in three-gallon containers in a polypropylene-covered greenhouse in Grand Haven, Mich. and under cultural practices typical of commercial *Weigela* production. During the production of the plants, day temperatures ranged from 18° C. to 27° C. and night temperatures ranged from 5° C. to 10° C. Plants of the new *Weigela* were three years old when the photographs and description were taken. In the following description, color references are made to The Royal Horticultural Society Colour Chart, 2015 Edition, except where general terms of ordinary dictionary significance are used.

Botanical classification: *Weigela florida* 'SMNWFG'.

Parentage:

*Female, or seed, parent*.—Unnamed proprietary selection of *Weigela florida*, not patented.

*Male, or pollen, parent*.—Unknown proprietary selection of *Weigela florida*, not patented.

Propagation:

*Type*.—By softwood stem cuttings.

*Time to initiate roots, summer*.—About 15 days at temperatures about 18° C. to 27° C.

*Time to produce a rooted young plant, summer*.—About two months at temperatures about 18° C. to 27° C.

*Root description*.—Fine; fibrous; typically white in color, actual color of the roots is dependent on substrate composition, water quality, fertilizer, substrate temperature and physiological age of roots.

*Rooting habit*.—Freely branching; dense.

Plant description:

*Plant and growth habit*.—Perennial shrub; upright to outwardly spreading and uniformly mounding plant habit; vigorous growth habit and rapid growth rate.

*Branching habit*.—Freely branching habit with about 30 lateral branches developing per plant; pinching enhances lateral branch development; dense and bushy plant form.

*Plant height*.—About 60 cm.

*Plant diameter*.—About 100 cm.

Lateral branch description:

*Length*.—About 50 cm.

*Diameter*.—About 5 mm.

*Internode length*.—About 6 cm.

*Texture*.—Slightly pubescent along longitudinal ridges; with development becoming less pubescent.

*Strength*.—Strong.

*Aspect*.—About 30° to 70° from vertical.

*Color*.—Close to 144C tinged with close to 199A.

Leaf description:

*Arrangement*.—Opposite; simple.

*Length*.—About 5 cm to 7 cm.

*Width*.—About 2.5 cm to 3.5 cm.

*Shape*.—Elliptic.

*Apex*.—Acuminate.

*Base*.—Cuneate.

*Margin*.—Serrulate.

*Texture, upper surface*.—Slightly pubescent; coriaceous.

*Texture, lower surface*.—Slightly pubescence along venation; prominent venation; coriaceous.

*Venation pattern*.—Pinnate.

*Color*.—Developing leaves, upper and lower surfaces: Close to N144A tinged with close to 165A. Fully expanded leaves, upper and lower surfaces: Close to 147A tinged with close to 200A; venation, close to 144C; when exposed to high light conditions, upper surface will be more heavily tinged with dark reddish brown.

*Petioles*.—Length: About 4 mm. Diameter: About 3 mm. Texture, upper and lower surfaces: Somewhat pubescent. Color, upper surface: Close to 147A tinged with close to 200A. Color, lower surface: Close to 147A.

Flower description:

*Flower arrangement and habit*.—Salverform flowers arranged in terminal clusters or in small panicles each with about six to twelve flowers; about 100 to 150 flowers develop per lateral stem during the flowering season; flowers face upright to outwardly and drooping.

*Fragrance*.—None detected.

*Natural flowering season*.—Plants of the new *Weigela* flower remontantly during the spring and summer in Grand Haven, Mich.; flowers not persistent.

*Flower buds*.—Length: About 2.5 cm. Diameter: About 5 mm. Shape: Obovate to spatulate. Color: Close to 64B.

*Flower diameter*.—About 2.75 cm.

*Flower depth*.—About 3.5 cm.

*Flower throat diameter*.—About 1.25 cm.

*Flower tube length*.—About 3 cm.

*Flower tube diameter, proximally*.—About 3 mm.

*Corolla*.—Arrangement: Salverform; five petals fused into a tube with separate petal lobes. Petal lobe length: About 1 cm. Petal lobe width: About 1.25 cm. Petal lobe shape: Roughly reniform. Petal lobe apex: Obtuse, occasionally notched. Petal lobe margin: Crenate; undulate and ruffled. Petal texture, upper and lower surfaces: Smooth, glabrous; delicate. Throat texture: Smooth, glabrous. Tube texture: Glabrous, some creasing. Color: Developing petal lobes, upper surface: Close to 70C. Developing petal lobes, lower surface: Close to 64B. Fully expanded petal lobes, upper surface: Close to 64B, occasionally with a medial stripe, close to 64C; venation, close to 64B. Fully expanded petal lobes, lower surface: Close to 64C; venation, close to 64C. Throat: Close to 64C; venation, close to 64C. Tube: Close to 64C; venation, close to 64C.

*Sepals*.—Quantity per flower: Five in a single whorl, fused at the base; calyx campanulate. Length: About 1 cm. Width: About 1 mm. Shape: Narrowly triangular, elongated. Apex: Acute. Margin: Entire. Texture, upper and lower surfaces: Smooth; glabrous. Color, upper and lower surfaces: Close to 200A.

*Peduncles*.—Length: About 6 cm. Diameter: About 3 mm. Strength: Strong. Aspect: About 90° from lateral branch axis. Texture: Slightly pubescent. Color: Close to 144C tinged with close to 199A.

*Pedicels*.—Length: About 2 cm. Diameter: About 2 mm. Strength: Strong; somewhat flexible. Aspect: About 30° to 80° from peduncle axis. Texture: Smooth, glabrous. Color: Close to 200A.

*Reproductive organs*.—Stamens: Quantity and arrangement: Five per flower. Filament length: About 1 cm. Filament color: Close to 73B. Anther shape: Narrowly oblong. Anther size: About 5 mm. Anther color: Close to 158B. Pollen amount: Moderate. Pollen color: Close to 158B. Pistils: Quantity: One per flower. Pistil length: About 3.5 cm. Style length: About 3 cm. Style color: Close to 73B. Stigma shape: Peltate to globular, lobed. Stigma color: Close to 158C. Seeds and fruits: To date, seed and fruit development has not been observed on plants of the new *Weigela*.

Garden performance: Plants of the new *Weigela* have exhibited good garden performance and to tolerate wind, rain and temperatures ranging from −31° C. to 38° C.

Pathogen & pest resistance: To date, plants of the new *Weigela* have not been observed to be resistant to pathogens and pests common to *Weigela* plants.

It is claimed:

1. A new and distinct *Weigela* plant named 'SMNWFG' as illustrated and described.

* * * * *